United States Patent
Cowper et al.

(10) Patent No.: US 9,637,720 B2
(45) Date of Patent: May 2, 2017

(54) METHOD FOR MULTIPLYING PHYTOBENEFICAL MICROORGANISMS

(71) Applicants: FLORENTAISE, St Mars du Desert (FR); NIXE, Valbonne (FR)

(72) Inventors: Jerome R. Cowper, Moncrabeau (FR); Renaud H. Canaguier, Grasse (FR); Helene L. Reynaud, Tanneron (FR)

(73) Assignees: FLORENTAISE, St Mars du Desert (FR); NIXE, Valbonne (FR)

( * ) Notice: Subject to any disclaimer, the term of this patent is extended or adjusted under 35 U.S.C. 154(b) by 4 days.

(21) Appl. No.: 14/362,292

(22) PCT Filed: Dec. 3, 2012

(86) PCT No.: PCT/FR2012/052776
§ 371 (c)(1),
(2) Date: Jun. 2, 2014

(87) PCT Pub. No.: WO2013/079887
PCT Pub. Date: Jun. 6, 2013

(65) Prior Publication Data
US 2014/0311199 A1    Oct. 23, 2014

(30) Foreign Application Priority Data

Dec. 2, 2011    (FR) ..................... 11 61099

(51) Int. Cl.
| | | |
|---|---|---|
| *C12N 1/14* | (2006.01) | |
| *C12N 1/22* | (2006.01) | |
| *A01N 63/04* | (2006.01) | |
| *C05F 11/08* | (2006.01) | |
| *C05F 17/00* | (2006.01) | |

(52) U.S. Cl.
CPC .............. *C12N 1/14* (2013.01); *A01N 63/04* (2013.01); *C05F 11/08* (2013.01); *C05F 17/0027* (2013.01); *C12N 1/22* (2013.01); *Y02P 20/145* (2015.11); *Y02W 30/43* (2015.05)

(58) Field of Classification Search
None
See application file for complete search history.

(56) References Cited

U.S. PATENT DOCUMENTS

| 4,642,241 | A | * | 2/1987 | Noguchi | ............... | A23L 1/0076 |
| | | | | | | 426/516 |
| 5,087,400 | A | * | 2/1992 | Theuveny | ............ | A01G 31/001 |
| | | | | | | 241/28 |
| 2004/0136964 | A1 | | 7/2004 | Gay et al. | | |

FOREIGN PATENT DOCUMENTS

| CA | WO 2010108267 A1 | * | 9/2010 | ............. A01N 63/04 |
| EP | 0147349 | | 7/1985 | |
| EP | 0324689 | | 7/1989 | |
| EP | 0947130 | | 10/1999 | |
| EP | 1281753 | | 2/2003 | |
| EP | 1400586 | | 3/2004 | |
| EP | 1876232 | | 1/2008 | |
| FR | 1158555 | | 6/1958 | |
| FR | EP 0147349 A1 | * | 7/1985 | ........... A01G 9/1086 |
| FR | 2776470 | | 10/1999 | |
| FR | EP 1876232 A1 | * | 1/2008 | ............ A01N 63/04 |
| GB | 1573850 | | 8/1980 | |
| JP | 2006035150 | | 2/2006 | |
| WO | 2009/083819 | | 7/2009 | |

OTHER PUBLICATIONS

Singh et al., "EVect of substrates on growth and shelf life of Trichoderma harzianum and its use in biocontrol of diseases", Bioresource Technology 2007, vol. 98, pp. 470-473.*
International Search Report; PCT/FR2012052776, dated Mar. 6, 2013 (4 pages—submitted Jun. 2, 2014).
Harman et al.: "*Trichoderma* Species—Opportunistic, Avirulent Plant Symbiontis"; Nature Reviews/Microbiology, 2004, vol. 2, pp. 43-56.
Mandels et al.: "Induction of Cellulase in trichoderma viride as influenced by Carbon sources and metals"; Biology Branch, Pioneering Research Division, U.S. Army Quartermaster Research and Development Center, Natick, MA, 1957, pp. 269-278.
J.G. Menzies : "A strain of Trichoderma viride pathogenic to germinating seedlings of cucumber, pepper and tomato"; Plant Pathology, 1993, vol. 42, pp. 784-791.
R. Weindling: "Tricoderma lignorum as a parasite of other soil fungi"; Phytopathology; 1932, vol. 22, pp. 837-845.
Tengerdy et al.: "Solid substrate fermentation"; Trends in Biotechnology, 1985, vol. 3, pp. 96-99.
Noguchi et al.: "New food proteins, Extrusion processes and Products in Japan" In: Proceedings of the World Congress on Vegetable Protein Utilization in Human Foods and Animal Feedstuffs; American Oil Chemists' Society, 1989, pp. 373-380.
Rao et al.: Biomass protein formation by filamentuous fungi on woody substrates; Biotechnology letters, 1984, vol. 6, pp. 461-464.
S. Roussos: "Croissance de trichoderma harzianum par fermentation en milieu solid: physiologie, sporulation et production de cellulases"; 1987, pp. 125-131, (186 pages submitted, with English Abstract on p. 14).

* cited by examiner

*Primary Examiner* — Renee Claytor
*Assistant Examiner* — Michelle F Paguio Frising
(74) *Attorney, Agent, or Firm* — Hamre, Schumann, Mueller & Larson, P.C.

(57) ABSTRACT

The invention relates to a method for multiplying a strain of *Trichoderma*, which includes the preparation of substantially contaminant-free culture media, containing disinfected wood fibers obtained by means of a twin-screw extruder, the amplification of *Trichoderma* via a series of steps for manufacturing a primary inoculum and then a secondary inoculum from said primary inoculum, and the multiplication of the microorganisms in each step, wherein the multiplication of the propagules reaches $2 \times 10^4$ to $10^5$.
The invention also relates to a plant growing medium containing a secondary inoculum of *Trichoderma*.

16 Claims, 2 Drawing Sheets

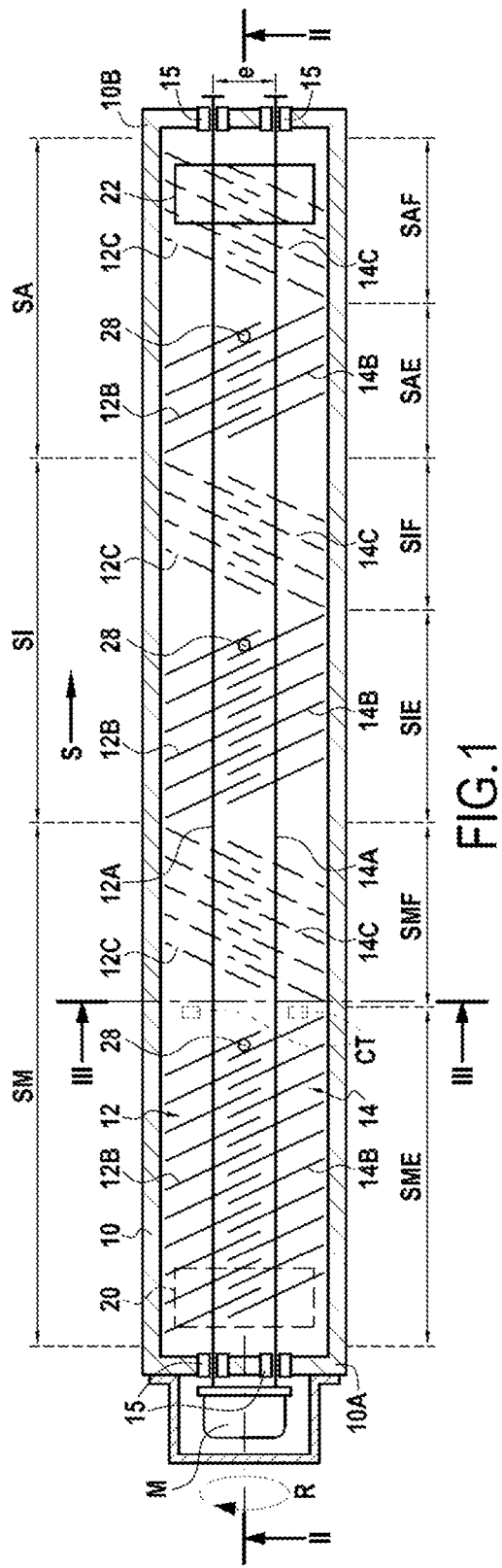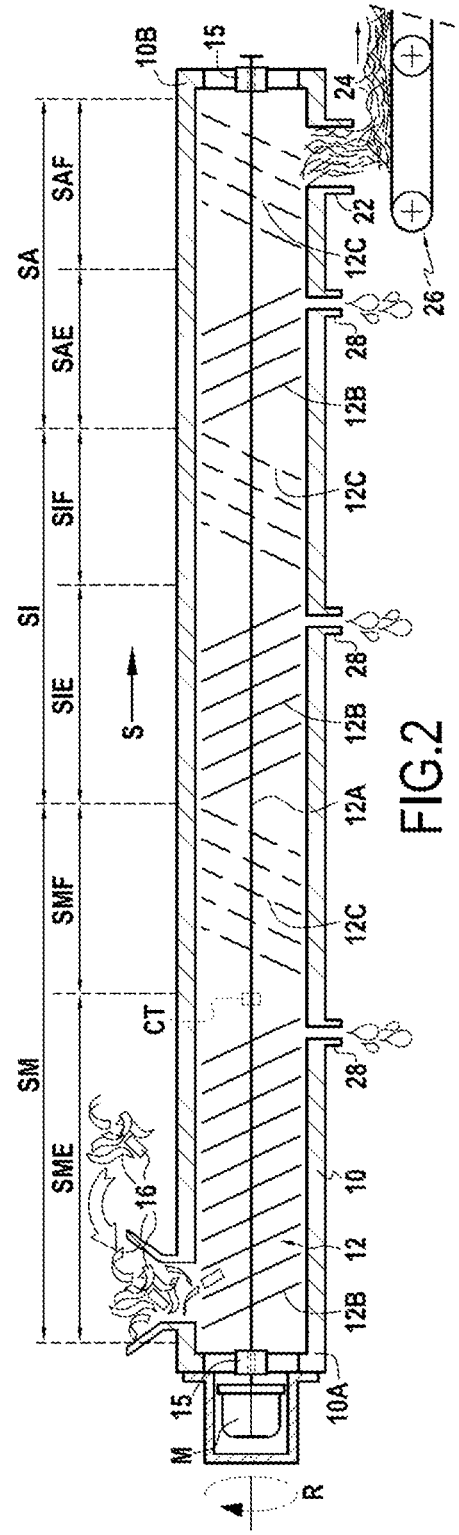

METHOD FOR MULTIPLYING PHYTOBENEFICAL MICROORGANISMS

FIELD OF THE INVENTION

The present invention relates to the field of growing supports. More particularly, the invention relates to a method for multiplying phytobeneficial microorganisms, in particular fungal microorganisms. The invention also relates to a growing support containing the resulting microorganisms.

TECHNOLOGICAL BACKGROUND

The enrichment of industrial composts with useful microbial flora is of interest either for decontaminating plant growing substrates, or for improving the fertility thereof.

Various microorganisms and various bacteria are used as plant biocontrol agents.

Plant growth promoting microorganisms are called PGPMs. Symbiotic mycorrhizal fungi and certain species of *Trichoderma* that are mutually beneficial with plants are part of this category. Plant growth promoting rhizobacteria are called PGPRs. This category comprises, for example, useful *Pseudomonas* and *Bacillus*.

The *Trichoderma* genus is an agronomically important group since it comprises biocontrol-agent fungi, the mode of action of which has been the subject of a great deal of work. Recent studies in fact mention that this filamentous fungus has a capacity to intervene according to various mechanisms: mycoparasitism, antagonism (competition), antibiosis (production of antibiotics), root stimulation, growth stimulation by solubilization of fertilizing minerals, stimulation of plant natural defenses.

Fungi of the *Trichoderma* genus belong to the phylum Ascomycota, class Ascomycetes, family Hypocreales. They are microscopic fungi of which there are terrestrial species and marine species. They are found in decomposing wood, in plant residues and in all soils (forest humus, agricultural earths) (from 10 to 10 000 propagules/g in temperate or tropical soils). They colonize the roots of herbaceous and ligneous plants without any damage. In addition, this fungus can penetrate roots and promote development, nutrition and resistance to diseases. The species *atroviride* is one of the common species of *Trichoderma*.

Root colonization by *Trichoderma* sp. can increase root growth and development, crop yield, resistance to abiotic stresses and nutrient absorption and use (Harman G. E. et al., Nature Reviews/Microbiology, 2, 43-56, 2004).

When they exist, the effects of growth stimulation originate from the direct action of *Trichoderma* on plants and are not directly linked to antagonisms with pathogens. These effects are visible both on nondisinfected growing substrates and on sterile substrates. The growth stimulation mechanisms are poorly elucidated and could be due to the suppression of oxidative damage on the roots, to the secretion of growth factors by the fungus, to the inhibition of bothersome microflora and to the improvement of micronutrient transport.

The effects are unequal from one strain to another. Some strains have growth-stimulating effects, but others have inhibitory effects (for example, *Trichoderma viride* RF1, J. G. Menzies, Plant Pathology, 42, 784-791, 1993).

The antagonistic properties of *Trichoderma* are better documented than the stimulatory properties. The antagonistic potential of *Trichoderma* with respect to numerous pathogenic soil fungi of plants was discovered in the 1930s (Weindling R., *Trichoderma lignorum* as a parasite of other soil fungi, Phytopathology, 22, 837-845, 1932). The most obvious application is biological control in agriculture (biocontrol), including in biological agriculture where (EC) regulation No. 2092/91 provides for this use.

Generally, there are two ways to enrich a medium with microorganisms:
- by dilution in the medium of a sufficient amount of microorganisms from a concentrated preparation; or
- by inoculation of the medium and in situ multiplication of the microorganisms.

The first technique calls for production of microorganisms in a separate system. It applies well to microorganisms which have stable resistance forms (for example, spores, conidia or chlamydospores). The technique consists in diluting the microorganism obtained separately in a medium which must be compatible, and which may be capable of aiding its regeneration when a favorable condition occurs (for example, hydration, heating of the medium). Such a technique is described, for example, in patent application US 2004/0136964A1. Said document relates to a substrate containing a strain of *Trichoderma asperellum* for the biological control of *Fusarium* and of *Rhizoctonia*, said substrate being obtained from a mixture consisting of waste, purification sludge, peat, bark or compost.

The second technique applies to microorganisms capable of multiplying in the medium until exhaustion of the nutritive resources or degradation of the vital conditions, so as to subsequently give dormant forms termed resistance forms. The resistance forms which can regenerate the microorganisms fall into the category of propagules. This second technique makes it possible to obtain a medium rich in stable propagules. The exhaustion of the readily fermentable matter makes the medium not very suitable for the development of other microorganisms. The enrichment by in situ multiplication can apply to bacteria, yeasts and fungi, capable of living in wood fiber-based media. The multiplication also relates to the category of mycorrhizal fungi which are also saprophytes. The multiplication may also relate to symbiotic mycorrhizal fungi of plants, on condition that they are cultivated on host roots.

Contrary to the dilution technique, the in situ multiplication does not require large amounts of microorganisms produced under sterile conditions. The multiplication is obtained by virtue of the consumption of nutritive substances contained in or added to the substrate. The multiplication is, in principle, aerobic. The medium is considered to be "activated" when specific nutritive substances are added in order to promote multiplication. The specific nutritive substances added to the "activated" medium are partially or totally consumed by the end of the multiplication phase. This is reflected by a loss of mass and the production of volatile metabolites, in particular of carbon dioxide ($CO_2$) and of water ($H_2O$).

The in situ multiplication technique comprises a phase of preparing the medium, with if necessary a disinfection, the addition of a sufficient amount of primary inoculum of microorganisms, the microorganism multiplication period, the appearance of the resistance forms and the maturation. Each step has a variable duration depending on the conditions and the microorganisms used. The multiplication can be carried out via successive enrichment cycles, the product of a multiplication cycle serving to inoculate a larger amount of medium. Cycle after cycle, the successive multiplication media can become increasingly simple and the multiplication conditions less and less severe. This makes it possible to obtain a good yield without using laborious production techniques. The stepwise technique improves the biomass yield and reduces the loss of substrate consumed for the growth of the microorganisms.

The in situ multiplication also makes it possible to reduce the bothersome microorganisms during the production of the compost by virtue of the introduction of competition. The propagules obtained by the multiplication technique are more stable than microorganisms added after the production of the compost. The compost obtained by means of the multiplication process may contain secondary metabolites released during the fermentation. The secondary metabolites of certain species of fungi (*Trichoderma*) and bacteria (*Pseudomonas*) are useful to plants, either because they decontaminate and detoxify the substrates, or because they stimulate growth.

In practice, the microorganisms that are useful to plants live in the rhizosphere or in the immediate proximity of the rhizosphere and benefit, for their nutrition, from the root exudates and the plant residues. Certain microorganisms, such as *Trichoderma*, live saprophytically in the soil or at the surface, on dead plant remains.

Various sorts of fibers are favorable to the growth of microorganisms; mention may in particular be made of wood fiber, palm fiber and the various plant fibers used in agricultural, textile or insulation applications. Aerated and fibrous materials, of plant origin, made of shavings, leaves or straw, are also suitable.

Patent applications EP-A-0 147 349 and FR-A-2 776 470 describe a culture medium based on wood fibers obtained by steam cooking and defiberizing, according to processes encountered both in the paper-making industry and in the chipboard industry. As indicated in patent application FR-A-2 776 470, the defiberizing is conventionally carried out by means of a disk grinder, using wood shavings from which the fibers are "extracted" by shearing at high temperature.

However, it has been noted by the applicant, following numerous tests, that the methods described in the above-mentioned documents have a tendency to cause cooking of the wood similar to the beginnings of roasting or to thermostabilization, the consequence of which is a reduction in the hydrophilicity and in the water retention capacity of the wood fibers produced. These drawbacks make the wood fibers not very conducive to an appropriate multiplication of microorganisms.

It is therefore desirable to be able to have wood fibers capable of promoting the multiplication of microorganisms, in particular of the *Trichoderma* genus, which are free of the drawbacks mentioned above.

It is also desirable to be able to have a culture medium which is suitable for multiplying such microorganisms, and which makes it possible to obtain a growing support conducive to the growing of plants.

DESCRIPTION OF THE INVENTION

It has now been found, and this is the basis of the invention, that it is possible to multiply microorganisms of the *Trichoderma* genus using a particular culture medium containing wood fibers for preparing a plant growing support.

Thus, according to a first aspect, the invention relates to a method for in situ multiplication of microorganisms of the *Trichoderma* genus, which comprises steps of disinfection, multiplication and amplification in steps:

the disinfection of the wood fiber during the production thereof immediately gives a substrate conducive to the culturing of *Trichoderma*, in a single step. The *Trichoderma* can be grown on wood shavings, but sterilization is necessary after production of the shavings. In the case of the fiber, production and sterilization are simultaneous;

the in situ multiplication of the *Trichoderma* fungus makes it possible to inoculate the plant growing support with useful microorganisms and to limit the level of contaminants. The in situ multiplication makes it possible to provide only a small amount of microorganisms compared with that which will be contained in the final product. The microorganisms multiply spontaneously by virtue of the particular composition of the growing support;

the amplification of the *Trichoderma* fungus via successive steps avoids the disinfection of large masses of matter. The multiplication conditions are less and less severe over the course of the steps. This method differs from the bulk inoculation of the entire plant growing support.

According to one embodiment of the invention, the method comprises:

the inoculating, with a stock suspension of *Trichoderma* propagules, of a sterilized culture medium containing between approximately 25% and approximately 50% by weight of wood fibers and also nutritive substances, water and, optionally, a pH modifier, said fibers having an air content by volume included in the range of from approximately 55% to approximately 90%, said medium being substantially free of fungal contaminants and having a bacterial contaminant content of less than or equal to $10^2$ CFU/g;

the culturing of the inoculated culture medium so as to obtain a primary inoculum in which the multiplication of the propagules reaches $2 \times 10^4$ to $10^5$.

It is particularly important to eliminate the fungal contaminants from the culture medium and to reduce the bacterial content thereof to below $10^2$ CFU/g. The elimination of the autochthonous *Aspergillus* and *Trichoderma* is in particular necessary since some strains of these fungi can compete with the inoculated microorganisms. The disinfected medium is particularly conducive to the inoculation and growth of the useful microorganisms. The inoculated microorganisms do not encounter competing organisms and can grow freely and rapidly. Preferably, the culture medium is sterilized by autoclaving under the usual conditions (121° C., approximately 30 min) before being inoculated and then incubated.

Advantageously, the final concentration of propagules of the primary inoculum is in the range of from approximately $10^8$ to approximately $10^{10}$ propagules/g.

Also advantageously, the culturing of *Trichoderma* comprises an incubation period of at least two weeks.

According to another embodiment, the method in accordance with the invention also comprises:

the preparation of a second culture medium containing wood fibers which have been disinfected, in particular by heating, said wood fibers having an air content by volume included in the range of from approximately 55% to approximately 90%;

the inoculation of said culture medium with 0.001% to 5% by weight of the primary inoculum;

the culturing of the culture medium thus inoculated so as to obtain a secondary inoculum. Advantageously, the final concentration of propagules in the secondary inoculum is in the range of from approximately $10^7$ to approximately $10^9$ propagules/g.

In a second aspect, the invention also relates to a method for preparing a secondary inoculum of *Trichoderma*, which comprises:

the preparation of a culture medium containing wood fibers which have been disinfected, in particular by heating, said wood fibers having an air content by volume included in the range of from approximately 55% to approximately 90%;

the inoculation of said culture medium with 0.001% to 5% of a primary inoculum of *Trichoderma*, which can be obtained as described above;

the culturing of the culture medium thus inoculated.

Advantageously, the final concentration of propagules in the secondary inoculum thus obtained is in the range of from approximately $10^7$ to approximately $10^9$ propagules/g.

Also advantageously, the culturing of the medium inoculated with the primary inoculum comprises an incubation period of at least two weeks.

Preferably, the culture medium used for preparing the primary inoculum, and the one used for preparing the secondary inoculum, each comprise wood fibers having an air content by volume included in the range of from approximately 60% to approximately 85%, preferably from approximately 70% to approximately 85%.

Advantageously, the wood fibers contained in the various culture media mentioned above are obtained by extrusion of wood shavings, in particular of wood chips, in an extruder, preferably a twin-screw extruder. In one embodiment of the invention, the wood shavings are extruded in the presence of wheat bran.

Entirely advantageously, the *Trichoderma* strain that it is desired to multiply is the *Trichoderma atroviride* MUCL45632 strain.

In a third aspect, the invention also relates to a culture medium as defined above with reference to the first aspect or to the second aspect of the invention.

In a fourth aspect, the invention also relates to a (primary or secondary) inoculum which can be obtained by means of the method described above.

In a fifth aspect, the invention relates to a plant growing support, in particular a compost, containing a secondary inoculum as defined above.

*Trichoderma* Production Conditions

The production of *Trichoderma* must be carried out both on a favorable culture medium and in an appropriate container.

The culture medium consists of fermentable materials, more particularly carbohydrates, lipids and proteins. Minerals, such as phosphorus, potassium, magnesium and sulfur, are required. There are also certain factors which promote growth and sporulation. Calcium, cobalt, iron, manganese and zinc (Mandels and Reese, 1957) are cited as elements favorable to growth and to cellulase production by *Trichoderma viride*.

It appears that *Trichoderma* fungi grow in acidic media. The acidification makes the culture medium selected for *Trichoderma* by inhibiting the growth of bacteria. Under these conditions, the addition of a pH modifier to the medium is advantageous; the modification may be of the order of 0.01 to approximately 6 pH units.

Patent GB1573850 describes the production of *Trichoderma* by culturing on cereals acidified to pH<4.5 and enriched with copper, in leaktight plastic bags which are periodically filled with air and from which the atmosphere is periodically removed. The periodic fractionation of the culture beds in order to promote homogeneity of the medium is also described.

Patent application EP-A-1 876 232, which relates in particular to the *Trichoderma atroviride* MUCL45632 strain, describes a culture medium which is suitable for the production of propagules of this fungus: "The culture medium essentially consists of a substrate of plant origin rich in polysaccharides such as starch, hemicellulose and cellulose. This substrate may consist, in a nonlimiting manner, of cereal (barley, oat) seeds or of seeds of leguminous plants (soya, lupin, beans), of by-products of the cereal industry (cereal bran, wheat germs, rice husks), of oil cakes from extraction of oleaginous plants (sunflower, cotton), of waste from the sugar industry and from the starch industry (beet pulp, sugar cane bagasse), of straw or of wood shavings. The plant substrate may be coarsely ground so as to form a mass permeable to water and to air. The medium may be supplemented with mineral elements useful for the growth of the fungus: nitrate, ammonium, ortho-phosphate, potassium, magnesium, calcium and trace elements. The pH will advantageously be acidified using an acid, preferably an inorganic acid, such as hydrochloric acid, sulfuric acid or ortho-phosphoric acid, between pH 2.7 and pH 4 and preferably between 2.7 and 3.3". These conditions are generally suitable for other *Trichoderma*, but those skilled in the art will, if necessary, adapt the culture conditions in order to obtain an optimum propagule yield.

The culturing of *Trichoderma* can be carried out in various containers: bags, boxes, cases or tanks, made of suitable materials, such as stainless steel, glass and plastics. Wood is also suitable, but it may be attacked by the *Trichoderma* and modified by the moisture.

The temperature for culturing the *Trichoderma* depends on the strains. Most *Trichoderma* grow starting from 12° C. and up to 35° C. The optimum growth temperatures are in the range of from 20 to 28° C. Carbohydrate consumption by the fungi causes heating of the medium (17 kJ/g of carbohydrate oxidized). This heating must be limited, since, above 36° C., the *Trichoderma* fungi begin to die. The heating is controllable in various ways:

By limiting the amount of readily oxidizable carbohydrates. This can be done by controlling the amount of simple sugars introduced into the load, or by using complex carbohydrates, also called fibers, requiring a succession of enzymatic hydrolyses before being available for oxidation. Starch (α-glucan), which rapidly hydrolyzes, is practically considered to be a simple sugar. Wood cellulose (β-glucan) is a complex sugar which oxidizes slowly.

By controlling the atmosphere around the culture medium. Reducing oxygen and increasing the carbon dioxide level limit the metabolic activity of the fungi. This can be obtained by placing the culture medium in a closed chamber and by curbing gas exchanges by this chamber with the outside air.

By controlling the initial amount of water and the water evaporation during culturing. Water evaporation is one of the methods for reducing the temperature of a culture medium. The lower the partial water pressure in the atmosphere (hygrometry), the greater the evaporation. The reduction of partial pressure is obtained, in particular, by increasing the gas exchanges with the outside air, as opposed to the principle of limiting gas exchanges set out above.

By promoting temperature exchanges through maximization of the surface area of the culture beds to the detriment of the volume, i.e., for example, by using containers having a flattened shape, such as flat bags or cushions.

By cooling the atmosphere or the culture medium.

The fungi consume oxygen during their growth (747 l O$_2$/kg of oxidized carbohydrates). Aeration is essential, but it may be limited to what is strictly necessary to obtain regular growth. Air is a vector of contaminants, it is therefore necessary to ventilate with purified air or to install systems which limit airborne contaminant propagation.

Wood Fibers

The wood fibers used in the context of the present invention are bulky and aerated, which allows good respiration of the microorganisms within the material; the fibers have an air content by volume included in the range of from approximately 55% to approximately 90%, preferably in the range of from approximately 60% to approximately 85%, more preferably in the range of from approximately 70% to approximately 85%. These wood fibers are advantageously obtained by extrusion of wood shavings, in particular of wood chips such as coniferous tree chips of paper quality from sapwood. The extrusion is carried out using a twin-screw extruder. The wood fibers obtained have the following physicochemical characteristics:

- a dry apparent density included in the range of from approximately 30 to approximately 100 kg/m$^3$, preferably in the range of from approximately 40 to approximately 100 kg/m$^3$, more preferably in the range of from approximately 50 to approximately 100 kg/m$^3$;
- a porosity included in the range of from approximately 88% to approximately 98% by volume;
- an air retention included in the range of from approximately 55% to approximately 80%, preferably in the range of from approximately 55% to approximately 70% by volume;
- a water retention included in the range of from approximately 18% to approximately 33%, preferably in the range of from approximately 23% to approximately 33% by volume;
- an electrical conductivity of less than or equal to approximately 0.5 mS/cm, preferably in the range of from approximately 0.2 to approximately 0.5 mS/cm, more preferably in the range of from approximately 0.3 to approximately 0.5 mS/cm.

The wood fibers used in the context of the present invention can be obtained by means of the method described in patent application FR 11 58555 filed on Sep. 26, 2011, the content of which is included in its entirety in the present application, and which is described hereinafter with reference to the appended FIGS. 1 to 3:

FIG. 1 is a diagrammatic view from above of a defiberizing apparatus for carrying out said method, in which the wall of the barrel is cut off;

FIG. 2 is a diagrammatic view corresponding to a sectional view of the apparatus of FIG. 1 in the plane II-II of FIG. 1, the parts of the screw 14 present in this plane being omitted;

Figure 3:
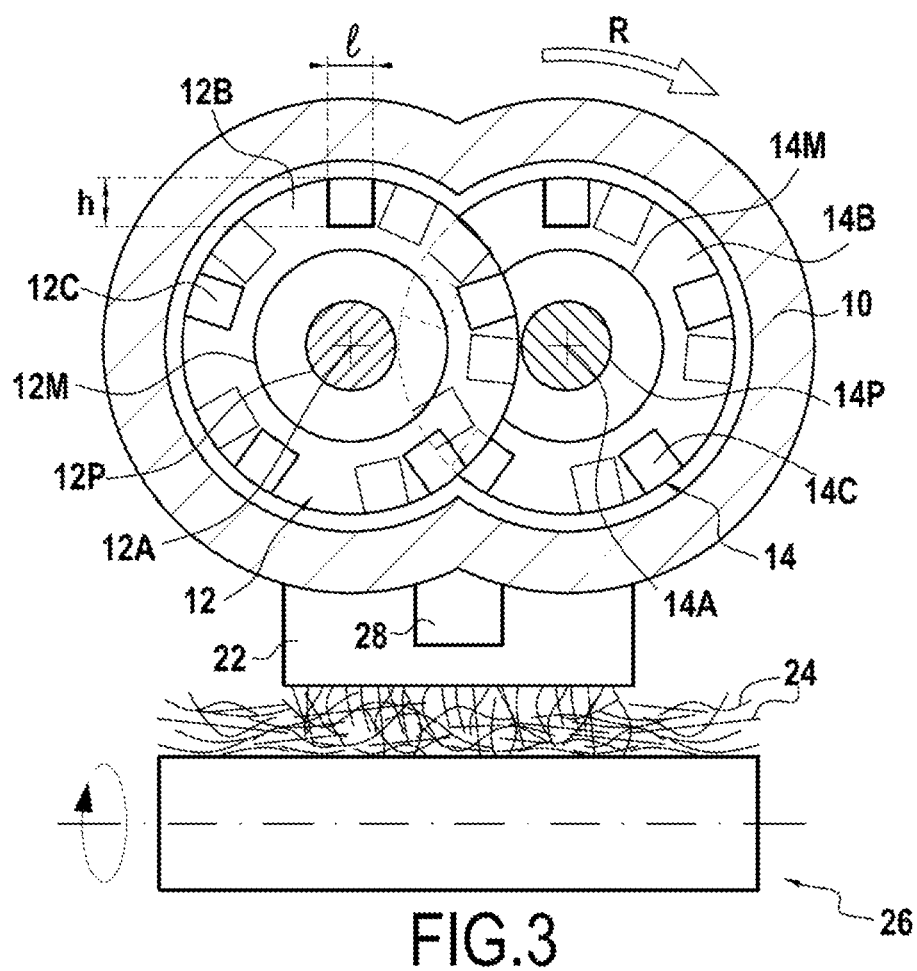
FIG. 3 is a section along the line III-III of FIG. 1.

According to this method, wood shavings (16) are introduced into a defiberizing barrel (10) containing two parallel screws (12, 14) driven rotationally so as to engage with one another via their respective threads (12B, 14B), said threads having successively, in the direction (S) from upstream to downstream, at least one upstream series and one downstream series of sections (SM, SI, SA) each comprising an upstream drive zone (SME, SIE, SAE) in which the shavings are driven in the downstream direction, and a downstream slowing down zone (SMF, SIF, SAF) through which the shavings are forced under the effect of drive provided by the upstream zone, these shavings thus being driven in the barrel (10) while being slowed down in the slowing down zones and while being converted into fibers (24) that can be recovered at the outlet of the defiberizing barrel (10), the residence time of the shavings in the barrel (10) being between 15 and 80 seconds, a pressure at least substantially equal to 90 bar being provided upstream of the downstream slowing down zone (SMF) of the upstream series (SM), such that a temperature of between 120° C. and 150° C. is reached in the barrel (10) without external provision of heat.

In one embodiment of this method, the residence time of the shavings in the barrel (10) is between 25 and 60 seconds.

In another embodiment of this method, the screws (12, 14) are rotated at a speed of between 250 and 400 revolutions per minute, preferably between 300 and 380 revolutions per minute. This rotation speed proves to be quite high for providing efficient defiberizing of the shavings. The length of the screws and the wood shavings load of the barrel can then be determined in order to ensure the desired residence time of the fibers in the barrel. For example, screws of which the length is between 1600 mm and 3000 mm will be chosen. If the length of the screws exceeds 2000 or 2300 mm, it is advantageous to provide for them to comprise, in addition to the upstream and downstream series of sections, an intermediate series, also having an upstream drive zone and a downstream slowing down zone.

In another embodiment of this method, in the upstream drive zones (SME, SIE, SAE), the shavings are brought into contact with direct-pitch threads, whereas, in the downstream slowing down zones (SMF, SIF, SAF), the shavings are brought into contact with inverted-pitch threads.

In another embodiment of this method, in the downstream slowing down zones (SMF, SIF, SAF), the shavings are passed through notches (12C, 14C) in the threads (12B, 14B).

In another embodiment of this method, each inverted-pitch thread of the downstream slowing down zone (SAF) of the downstream series (SA) comprises from 2 to 6 notches and the ratio R$_{sd}$ between the flow rate of exiting fibers and the sum of the cross sections of the notches of such a thread is between 60 and 80 mm$^2$/m$^3$, preferably between 70 and 75 mm$^2$/m$^3$ h$^{-1}$.

Thus, the notches being determined as indicated above, the feeding of the barrel with shavings, which determines the shavings load of the barrel, is carried out such that the ratio between the sum of the cross sections of the notches of a thread and the flow rate of exiting fibers is in the range indicated above. Under these conditions, a pressure of at least 90 bar is simply obtained, without requiring a complex barrel structure. The flow rate of exiting fibers is determined by measuring, according to standard NF EN 12580, the volume of fibers collected at the outlet of the barrel, expressed in m$^3$, in one hour.

The apparatus represented in the figures comprises a barrel 10 in which there are two screws 12, 14 which engage with one another. Indeed, the distance e between centers of the two screws is less than the external diameter of their threads. The shafts 12A and 14A of the screws 12 and 14 are driven rotationally by a motor M and supported rotationally by bearings, such as the bearings 15.

As is seen more clearly in FIG. 3, the external wall of the barrel has the shape of two portions of secant cylinders, each adapted to the diameter of the screws 12 and 14. The barrel has, preferably over its entire length, a hood which opens, forming one of its longitudinal walls so as to allow maintenance thereof and emptying thereof, if necessary.

The shavings or chips 16 which have to be defiberized, i.e. reduced to fibers, are loaded into the barrel via a feed 20, located at the upstream end 10A of the barrel and having, for example, the form of a hopper located on the upper face of the barrel, into which the shavings are conveyed by any appropriate means, for example by a screw conveyor, not represented.

At its downstream end 10B, the barrel has an outlet 22. It is, for example, a chute located at the lower face of the barrel and which allows the fibers 24 to fall by gravity onto a conveyor belt 26. This conveyor may be equipped with a tunnel (not represented), ventilated by a gas such as air, which is preferably filtered, so as to gradually cool the fibers while they are being conveyed.

The opening of the wall of the barrel formed at the feed 20 is advantageously symmetrical with respect to the median vertical plane between the axes 12A and 12B of the screws so as to ensure good distribution of the shavings over the two screws as soon as said shavings enter the barrel. Likewise, the opening formed at the outlet 22 of the barrel is advantageously symmetrical with respect to the same vertical plane.

Due to the rotation of the screws, the shavings are driven in the direction S from upstream to downstream.

Placed in the lower wall of the barrel are one or more extraction filters 28 which are used to extract the juices originating from the defiberizing or the water from washing the shavings, thus making it possible to regulate the final moisture content of the product. For example, these filters are placed at the upstream end of the slowing down zones which will subsequently be described.

The two screws 12 and 14 rotate in the same direction R and at the same rotation speed. Indeed, on each section of the screws facing each other, the threads of the two screws are in the same direction.

For each screw, the threads have an upstream series SM and a downstream series SA of sections. In the case in point, the threads also have an intermediate series SI located between the upstream series SM and the downstream series SA. Thus, the SM, SI and SA series are arranged successively from upstream to downstream of the barrel.

Each of these series itself comprises an upstream drive zone, respectively SME, SIE and SAE for the upstream, intermediate and downstream series, and also a downstream slowing down zone, respectively SMF, SIF and SAF for the upstream, intermediate and downstream series. These drive and slowing down zones are, respectively, described as upstream and downstream because, for each series, the drive zone is upstream of the slowing down zone in the direction S of progression of the shavings undergoing defiberizing.

It is seen that, in the drive zones SME, SIE and SAE, the threads 12B and 14B of the screws 12 and 14 are direct-pitch threads. This means that, via the rotation of the screws in the direction R, these threads naturally advance, in the downstream direction, the material which is located between them. On the other hand, in the slowing down zones SMF, SIF and SAF, the threads 12B and 14B are inverted-pitch threads, i.e. the rotation of the screws in the direction R tends to cause the material located between them to back up in the upstream direction.

As a result of this, for each series, the material undergoing defiberizing has a tendency to agglutinate at the interface between the drive zone and the slowing down zone. In order to even so allow the material to be conveyed in the downstream direction through each slowing down zone, the threads of the slowing down zones have interruptions or notches 12C, 14C. Thus, these notches form bottleneck zones through which the material is forced to pass, under the effect of the pushing exerted, upstream, by the material driven in the downstream direction by the upstream drive zone.

The notches can be seen more clearly in FIG. 3, which is a vertical section taken immediately upstream of a slowing down zone (in the case in point, the slowing down zone of the upstream series SM) and shows the organization of a slowing down zone. In the case in point, for the slowing down zone of each of the two screws 12 and 14, each thread comprises five identical notches, respectively 12C and 14C evenly distributed angularly.

The geometric axes of the screws are marked by the references 12A and 14A, which are the axes of rotation of their supporting shafts, respectively 12P and 14P. Since the screw sections can advantageously be dismantled, their threads are borne by sleeves, respectively 12M and 14M, which are mounted on the supporting shafts and made to rotate together with said shafts by any appropriate means, for example by means of axial grooves (not represented).

For each thread, the notches are radially delimited between the external radial periphery of the thread and its internal radial periphery, delimited by the external surface of the sleeve, respectively 12M and 14M. For example, the external diameter of each screw, delimited by the external radial periphery of its thread, is 240 mm, the radial height h of a notch is 44 mm and the width of a notch is 16 mm. For one thread, i.e. by following a thread of the screw over an angle of 360°, a sum of the cross sections of the notches of this thread of 5×44×16=3520 mm$^2$ is thus achieved.

Advantageously, in a slowing down zone of the screw 12 or 14, the notches 12C or 14C of two consecutive threads of the same screw are slightly angularly offset. To illustrate this feature in FIG. 3, the notches of the threads which are located first starting from the plane of section have been represented in thick lines, while the position of the notches which equip the threads located immediately downstream of these first threads have been shown in thin lines. In the case in point, the angular offset is about 10 to 20 degrees and it is oriented in the direction of rotation R of the screws, such that a line connecting two corresponding notches of two adjacent threads is oriented in the same direction as the direct-pitch threads.

The feeding of the apparatus is carried out continuously and the feed flow rate is regulated so as to adhere to the pressure and temperature parameters previously mentioned.

Thus, the apparatus advantageously comprises at least one temperature sensor CT located upstream of the downstream slowing down zone SMF of the upstream series (in the region of the plane of section III-III). A table of correspondence between the temperature and the pressure can be established. Thus, an increase in the temperature revealed by the temperature sensor CT may reveal a risk of pressure increase which is too great. In this case, the apparatus can be regulated by reducing the wood shavings feed flow rate. Direct measurement of the pressure can also be provided for, by means of a pressure sensor CP located in the same region as the temperature sensor CT. The measurements of these sensors (at least that of the temperature sensor CT) can be provided at input to a microprocessor which gives a command to the wood shavings feed system, for example a worm screw, as previously indicated. If no direct pressure measurement is available, the microprocessor may, in its memory, have a temperature/pressure correspondence table.

If a direct measurement of the pressure is carried out, the microprocessor may control the wood shavings feed system on the basis of the two temperature/pressure data with which it is provided. For a given wood species and a known moisture content, a relationship can be established between, on the one hand, the pressure and temperature parameters and, on the other hand, the electric power consumed by the motor which rotates the screws (or the electric current delivered, if the electric voltage is constant, as is often the case). This relationship can be determined empirically by means of tests. This relationship being known, it is possible to obtain the desired pressure and temperature parameters by regulating the wood shavings feed so as to consume a target power.

An essential aspect of the method of enrichment by multiplication on wood fiber is the need to cool the wood fiber after production thereof. The cooling must be carried out under conditions which preserve the initial microbial cleanliness.

The wood which passes through the screw extruders or through the steam grinders is heated to temperatures which can reach 150° C. At the outlet of the machines, the expansion and evaporation of water lower the temperature. The measurements indicate temperatures of 50 to 80° C. at machine outlet. The optimum temperature for incorporating the microorganisms depends on the species used. Some thermophilic bacteria withstand temperatures of 50 to 60° C. without difficulty, with no modification of the multiplication capacity. This is observed with bacteria such as *Bacillus* or *Paenibacillus*. For the other microorganisms, temperatures above 45° C. are critical for the survival of the resistance forms.

The inoculation of a substrate containing wood fibers can be carried out only after having lowered its temperature below the limiting temperature for growth of the inoculated microorganisms. For *Trichoderma*, generally, the limit is at 37° C.

The cooling of the wood fiber requires either passing it through a stream of cold filtered air, or a period where it is left to stand in a closed container for a period of time sufficient for the temperature to be below 37° C. at any point.

Transporting the hot wood fiber on a transporter belt placed in a tunnel ventilated with filtered air is an appropriate method for cooling large amounts of sterile hot fibers, without risk of recontamination.

Culture Medium

In one embodiment of the invention, the culture medium used for preparing the primary inoculum, and the one used for preparing the secondary inoculum, may be sterilized directly by passing them through a twin-screw extruder, in which case no autoclaving step is necessary. In this embodiment, wood shavings, in particular wood chips, are extruded in a twin-screw extruder, into which the various constituents of the culture medium (in particular the nutritive substances, the pH modifier and the water) are introduced in the form of a liquid mixture. The extrusion temperature is advantageously about 120° C. A sterilized culture medium is thus obtained.

Multiplication of *Trichoderma* In Situ

Generally, during the in situ multiplication, the production begins with a stock culture of microorganisms that is obtained in the laboratory on conventional microbiology media. This stock culture is used to prepare a primary inoculum, obtained by growth of the microorganisms on a medium based on plant fibers "activated" by adding nutrients based on carbohydrates and minerals, and suitably disinfected. The microorganisms multiply between $10^4$ and $10^5$ times, in terms of number of propagules, within the primary inoculum. The primary inoculum is an intermediate intended either for inoculating composts or, preferably, for producing a secondary inoculum.

The secondary inoculum is based on plant fibers optionally "activated" with carbohydrates and minerals. The secondary inoculum must be microbiologically clean, without necessarily being sterile. The multiplication in the secondary inoculum is lower, $10^3$ to $10^5$ times, in terms of number of propagules. This secondary inoculum is itself intended for inoculating composts.

In the context of the invention, two levels of *Trichoderma* amplification are suitable for achieving a total multiplication factor of from 200 000 to 1 000 000 between the stock culture and the final compost.

The stock culture is prepared in Petri dishes on a sterilized medium, conducive to the multiplication of *Trichoderma* fungi. Suitable media are potato dextrose broth (PDB), potato dextrose agar (PDA), malt agar (MA or MA2) or McFadden and Sutton rose bengal/streptomycin/formol (RB-S-F) medium.

The primary inoculum is prepared in the laboratory. The stock culture is used to prepare a suspension of propagules in sterile water. The suspension is incorporated into the activated culture medium intended to form the primary inoculum. The activated culture medium is prepared with sterilized starting materials. It comprises wood fibers, and preferably nutritive substances, pH modifiers and water. If the culture medium is not directly sterilized as indicated above, the sterilization is carried out by heating at a high temperature (121° C.), under water vapor pressure, in an autoclave. The incubation of the primary inoculum requires 2 to 3 weeks to obtain propagules which are at the optimum of their viability. If it is not contaminated by other microorganisms, the primary *Trichoderma* inoculum can be stored at a temperature below 22° C. for several months. Storage at 4° C. to 6° C. is even better. In the primary inoculum, the multiplication observed commonly reaches $2 \times 10^4$ to $10^5$. The final propagule concentration is in the range of from $10^8$ to $10^{10}$ propagules/g.

The secondary inoculum is produced in a production unit, in a clean but non-sterile environment, from materials disinfected by heating. The defiberizing of the wood shavings in a screw grinder (typically an extruder) which produces mechanical heating (100-120° C.), or in a disk grinder under vapor pressure (3 to 8 bar), results in the obtaining of disinfected wood fibers. The wood fiber must be cooled, before inoculation, to a temperature compatible with the survival of *Trichoderma*, therefore below 37° C. The culture medium (containing the "disinfected" wood fibers) is itself disinfected, for example by acidification and/or addition of sulfite (or alternatively, by sterilizing filtration, ultraviolet radiation, heating). It is also possible, as for the preparation of the primary inoculum, to disinfect the culture medium by passing it through a twin-screw extruder. The incubation of the secondary inoculum requires 2 to 3 weeks at a temperature between approximately 20° C. and approximately 25° C. Stability tests at a temperature of 22° C. over long periods of 5 months have also been carried out, still with stability of the *Trichoderma* spore viability. The multiplication in the secondary inoculum generally reaches $10^3$ to $10^4$. The final concentration in the secondary inoculum is in the range of from $10^1$ to $10^9$ propagules/g.

The secondary inoculum can then be incorporated into commercial composts in a proportion of from 0.02% to 0.5% w/w, i.e. approximately 0.5 to 2 m³ of secondary inoculum/ 1000 m³ final compost. The secondary inoculum can be combined with agents for protecting *Trichoderma* during its incorporation into the composts. The objective is to obtain a final concentration of $10^4$ to $10^6$ propagules/g in the final compost. The optimal dosage depends on the *Trichoderma* strain used and on the desired effects. The appropriate concentration of *Trichoderma atroviride* MUCL45632 (described in patent application EP-A-1 876 232) is $10^5$ propagules/g with a tolerable minimum of $10^4$ propagules/g.

The invention is illustrated by the examples hereinafter, given purely by way of indication.

Example 1

Preparation of a Primary Inoculum

Preparation of the Stock Suspension

The *Trichoderma atroviride* MUCL45632 fungus is cultured in a Petri dish on an appropriate medium (PDA) so that it produces spores. The spores are recovered in sterile water by scraping the surface of the dish. A quantitative determination of the total spores in this suspension is carried out and the concentration is adjusted to $1 \times 10^7$ spores/ml of total *Trichoderma* spores using sterile water.

Preparation of the Culture Medium a) 217 g of wheat bran (used for animal feed) are mixed with 540 g of wood chips (dry matter: 60-70%) and this mixture is extruded in a KRO 200 twin-screw extruder available from the company Clextral, the characteristics of which are the following:
Length (mm): 1600
Compression zone: 2
Rotation: Co
Temperature: 120° C.
The wood fibers have (after extrusion) a dry apparent density of 40 kg/m³.
b) The following are mixed in a beaker:

| | |
|---|---|
| water | 722 g |
| vitamin C | 1.1 g |
| glycerol | 21.7 g |
| sodium sulfite | 0.65 g |
| 84% $H_3PO_4$ | 20.9 g |
| $CoCl_2$ | 0.003 g |

The liquid fraction b) is poured into the solid fraction a) and the mixture is homogenized. The mixture is poured into a 2 l polypropylene autoclave bag. After filling, the bag is sealed while leaving an opening of 7 cm closed with carded cotton. The bag is then autoclaved for 35 min at 121° C. after Autoclaving:
pH ⅕ vol: 3.1
Dry matter: 32.8%
Total weight: 1523 g Inoculation of the Medium 150 ml of *Trichoderma* stock suspension at $1 \times 10^7$ spores/ml are added to the bag, i.e. $1 \times 10^6$ spores/g of medium, and the mixture is homogenized.

Culturing

The bag is placed in an incubator regulated at 27° C. for 4 days, and then the temperature is maintained at 25° C. A needle connected to a feed of sterile air under pressure via a pipe is planted at the bottom of the bag opposite the opening closed with cotton, so as to provide 10 l/h of air during the culturing. After 7 days, the bags are mixed manually in order to stimulate sporulation. After 2 days, the filaments of the fungus begin to appear. At 4 days, the culture medium begins to heat up. A temperature of 28° C.-30° C. is reached. The culturing is left to take place for 21 days.

Observations at the End of Culturing

At the end of culturing, the following are measured:
pH ⅕ vol: 3.3
Dry matter: 32%

The viability and the degree of contamination of the culture medium are reported in table 1. The viable spores are counted according to standard NF ISO 7954.

TABLE 1

| Dosages | Total spores/g | Propagules/g | Bacterial contaminants (CFU/g) |
|---|---|---|---|
| 21 days of culturing | $1.8 \times 10^9$ | $1.0 \times 10^9$ | $3.8 \times 10^4$ |
| 1 month storage refrigerator | $2.0 \times 10^9$ | $1.1 \times 10^9$ | $3.3 \times 10^5$ |
| 2 months storage refrigerator | $1.8 \times 10^9$ | $1.2 \times 10^9$ | nd |
| 3 months storage refrigerator | $1.5 \times 10^9$ | $1.1 \times 10^9$ | $<10^4$ |
| 1 month storage ambient temperature | $2.1 \times 10^9$ | $2.2 \times 10^9$ | $2 \times 10^2$ |
| 2 months storage ambient temperature | $2.3 \times 10^9$ | $1.0 \times 10^9$ | $6.8 \times 10^3$ |
| 4 months storage ambient temperature | $2.5 \times 10^9$ | $1.4 \times 10^9$ | nd |
| 6 months storage ambient temperature | $1.3 \times 10^9$ | $1.6 \times 10^9$ | nd | nd = not determined

On reading this table, it is noted that the batches all retain a viability greater than or equal to $10^9$ spores/g after 3 months in a refrigerator at 5° C. It is also noted that the batches all retain a viability greater than or equal to $10^9$ propagules/g after 6 months at ambient temperature. It is preferable to obtain a product without contaminants, but the bacteria present in this test do not cause the *Trichoderma* viability to drop.

Example 2

Preparation of a Secondary Inoculum

Preparation of the Culture Medium a) 118 kg of wheat bran (used for animal feed) are mixed with 481 kg of wood chips (dry matter: 60-70%) and this mixture is extruded in a KRO 200 twin-screw extruder (cf. example 1).
b) The following are mixed in a tank:

| | |
|---|---|
| water | 483 kg |
| vitamin C | 0.966 kg |
| sodium sulfite | 0.240 kg |
| 84% $H_3PO_4$ | 7.77 kg. |

The mixing must be carried out in such a way as not to contaminate the future culture. The liquid fraction b) is poured into the solid fraction a) and the mixture is homogenized in a mixer.

Inoculation with the Primary Inoculum 133 g of sodium sulfite and the bag of primary inoculum of the previous example are added to 167 l of clean water. The suspension is homogenized and left to stand for 24 h. The suspension is poured into the mixer which contains the culture medium and everything is mixed together. The inoculation is carried out at $1 \times 10^6$ total spores/g of medium.

Culturing

The mixture is poured into 50 sealed 25 kg polypropylene bags with an opening closed with cotton and an injection of air. This system limits water loss. Alternatively, 50 woven 25 kg polypropylene bags may be used, but the medium dries out during culturing. The bags are separated from one another in order to avoid heating.

The culturing is carried out in a closed clean room at a temperature of between 19° C. and 25° C. Air currents are avoided and personnel passing through is limited to those strictly necessary. The culturing takes place for 21 days.

Observations at the End of Culturing in Sealed Bags

At the end of culturing, the fibers have turned green in color, signifying the presence of *Trichoderma* spores.

The viability and the degree of contamination of the culture medium are reported in table 2. The viable spores are counted according to standard NF ISO 7954.

TABLE 2

| Dosages | Total spores/g | Propagules/g | Bacterial contaminants (CFU/g) |
|---|---|---|---|
| 21 days of culturing | $8.8 \times 10^8$ | $1.1 \times 10^9$ | $7.8 \times 10^4$ |
| 1 month storage at 25° C. | $1.9 \times 10^9$ | $1.2 \times 10^9$ | $2.1 \times 10^5$ |
| 2 months storage at 25° C. | $2.2 \times 10^9$ | $1.1 \times 10^9$ | nd |
| 5 months storage at 25° C. | $1.6 \times 10^9$ | $1.0 \times 10^9$ | nd |
| 7 months storage at 25° C. | $9.0 \times 10^8$ | $6.7 \times 10^8$ | nd | nd = not determined

Observations at the End of Culturing in Woven Bags

At the end of culturing, the following are measured:

Dry matter 38.9% pH: 3.

The viability and the degree of contamination of the culture medium are reported in table 3. The viable spores are counted according to standard NF ISO 7954.

TABLE 3

| Dosage | Total spores/g | Propagules/g | Bacterial contaminants (CFU/g) |
|---|---|---|---|
| 21 days of culturing | $9.7 \times 10^8$ | $4 \times 10^8$ | $9.5 \times 10^2$ |

Example 3

*Trichoderma* Stability in the Starting Materials and the Compost

The stability and viability of the *Trichoderma* strain is a particularly noteworthy property which meets the expectations of users seeking products which can be transported and stored without risk of loss at ambient temperature and without the problem of observing the cold chain.

The tests on some starting materials and a commercial compost show that the *Trichoderma atroviride* MUCL45632 spores do not die when they are cultured, in the presence of the wood fibers of the invention, under temperate preserving conditions. The results are reported in table 4.

TABLE 4

| Dosages (propagules/g) | Theoretical | Start | 1 month of storage | 2 months of storage | 3 months of storage |
|---|---|---|---|---|---|
| fiber of the invention | $5 \times 10^6$ | $5 \times 10^6$ | $1.5 \times 10^7$ | $9.5 \times 10^6$ | $4 \times 10^6$ |
| white peat | $5 \times 10^6$ | $6.3 \times 10^6$ | $1.5 \times 10^6$ | $1.1 \times 10^5$ | $4.5 \times 10^4$ |
| coconut fiber | $5 \times 10^6$ | $1.7 \times 10^6$ | $2.5 \times 10^7$ | $1.7 \times 10^7$ | $9.6 \times 10^6$ |
| fresh bark | $5 \times 10^6$ | $4.7 \times 10^6$ | $2 \times 10^6$ | $3 \times 10^5$ | $6 \times 10^4$ |
| composted bark | $5 \times 10^6$ | $5.2 \times 10^6$ | $4.4 \times 10^5$ | $3.5 \times 10^5$ | $1.2 \times 10^5$ |
| commercial compost | $1 \times 10^7$ | $5.8 \times 10^6$ | $1 \times 10^6$ | $1.1 \times 10^5$ | $1.5 \times 10^4$ |

The invention claimed is:

1. A method for multiplying a strain of *Trichoderma*, which comprises:
   inoculating, with a stock suspension of *Trichoderma* propagules, of a first sterilized culture medium containing between approximately 25% and approximately 50% by weight of wood fibers, water, nutritive substances and a pH modifier, said fibers having an air content by volume included in the range of from approximately 55% to approximately 90%, said medium being free of fungal contaminants and having a bacterial contaminant content of less than or equal to $10^2$ CFU/g; and
   culturing the culture medium thus inoculated so as to obtain a primary inoculum in which the multiplication factor of the propagules reaches $2 \times 10^4$ to $10^5$;
   wherein said fibers are obtained by extrusion of wood shavings in a twin-screw extruder by a method comprising:
   introducing wood shavings into a defiberizing barrel containing two parallel screws driven rotationally so as to engage with one another via their respective threads, said threads having successively, in the direction from upstream to downstream, at least one upstream series and one downstream series of sections each comprising an upstream drive zone in which the shavings are driven in the downstream direction, and a downstream slowing down zone through which the shavings are forced under the effect of drive provided by the upstream zone, the shavings being driven in the barrel while being slowed down in the slowing down zones and being converted into fibers that can be recovered at the outlet of the defiberizing barrel, the residence time of the shavings in the barrel being between 15 and 80 seconds, a pressure at least about 90 bar being provided upstream of the downstream slowing down zone of the upstream series, such that a temperature of between 120° C. and 150° C. is reached in the barrel without external provision of heat to the defiberizing barrel.

2. The multiplication method as claimed in claim 1, in which the final concentration of propagules in the primary inoculum is in the range of from $10^8$ to $10^{10}$ propagules/g.

3. The method as claimed in claim 1, in which the culturing of the medium comprises an incubation period of at least two weeks.

4. The method as claimed in claim 1, which also comprises:
   preparing a second culture medium containing wood fibers as obtained in claim 1, said wood fibers having an air content by volume included in the range of from approximately 55% to approximately 90%;
   inoculating said second culture medium with 0.001% to 5% by weight of the primary inoculum; and culturing the culture medium thus inoculated so as to obtain a secondary inoculum in which the multiplication factor of the propagules reaches $10^3$ to $10^5$.

5. The method as claimed in claim 4, in which the final concentration of propagules in the secondary inoculum is in the range of from $10^7$ to $10^9$ propagules/g.

6. The method as claimed in claim 4, in which the culturing of the medium comprises an incubation period of at least two weeks.

7. The method as claimed in claim 1, in which the wood fibers have an air content by volume included in the range of from approximately 60% to approximately 85%.

8. The method as claimed in claim 7, in which the wood fibers have an air content by volume included in the range of from approximately 70% to approximately 85%.

9. The method as claimed in claim 1, in which the wood shavings are extruded in the presence of wheat bran.

10. The method as claimed in claim 1, wherein the wood shavings are extruded concomitantly with water, the nutritive substances and the pH modifier, thereby sterilizing the first culture medium.

11. The method as claimed in claim 1, in which the *Trichoderma* strain is the *Trichoderma atroviride* MUCL45632 strain.

12. A method for preparing a secondary inoculum of *Trichoderma*, which comprises:
    preparing a culture medium containing disinfected wood fibers, said wood fibers having an air content by volume included in the range of from approximately 55% to approximately 90%;
    inoculating said culture medium with 0.001% to 5% by weight of a primary inoculum of *Trichoderma* obtained by the method of claim 1, the propagule concentration of which is in the range of from $10^8$ to $10^{10}$ propagules/g; and
    culturing the culture medium thus inoculated so as to obtain a secondary inoculum, the propagule concentration of which is in the range of from $10^7$ to $10^9$ propagules/g;
    wherein said disinfected fibers are obtained by extrusion of wood shavings in a twin-screw extruder by a method comprising:
    introducing wood shavings into a defiberizing barrel containing two parallel screws driven rotationally so as to engage with one another via their respective threads, said threads having successively, in the direction from upstream to downstream, at least one upstream series and one downstream series of sections each comprising an upstream drive zone in which the shavings are driven in the downstream direction, and a downstream slowing down zone through which the shavings are forced under the effect of drive provided by the upstream zone, these shavings thus being driven in the barrel while being slowed down in the slowing down zones and while being converted into fibers that can be recovered at the outlet of the defiberizing barrel, the residence time of the shavings in the barrel being between 15 and 80 seconds, a pressure at least about 90 bar being provided upstream of the downstream slowing down zone of the upstream series, such that a temperature of between 120° C. and 150° C. is reached in the barrel without external provision of heat.

13. The method as claimed in claim 12, in which the culturing of the medium comprises an incubation period of at least two weeks.

14. The method as claimed in claim 12, in which the wood fibers have an air content by volume included in the range of from approximately 60% to approximately 85%.

15. The method as claimed in claim 14, in which the wood fibers have an air content by volume included in the range of from approximately 70% to approximately 85%.

16. The method as claimed in claim 12, in which the wood shavings are extruded in the presence of wheat bran.

* * * * *